(12) United States Patent  
Walsh et al.

(10) Patent No.: US 7,758,649 B2
(45) Date of Patent: Jul. 20, 2010

(54) REVERSIBLY DEFORMABLE IMPLANT

(75) Inventors: Christopher Walsh, Parkland, FL (US); Wyatt Drake Geist, Davie, FL (US)

(73) Assignee: Integrity Intellect Inc., Tamarac, FL (US)

( * ) Notice: Subject to any disclaimer, the term of this patent is extended or adjusted under 35 U.S.C. 154(b) by 58 days.

(21) Appl. No.: 11/462,609

(22) Filed: Aug. 4, 2006

(65) Prior Publication Data
US 2008/0033575 A1  Feb. 7, 2008

(51) Int. Cl.
*A61F 2/44* (2006.01)
(52) U.S. Cl. .................. 623/17.16; 623/17.11
(58) Field of Classification Search ................ 623/1.19, 623/1.25, 23.67, 8, 6.18, 17.11–17.16, 23.61, 623/16.11, 14.12, 18.11
See application file for complete search history.

(56) References Cited

U.S. PATENT DOCUMENTS

| | | | |
|---|---|---|---|
| 3,640,282 A | 2/1972 | Kamen et al | |
| 3,875,595 A | 4/1975 | Froning | |
| 3,889,685 A | 6/1975 | Miller, Jr. et al. | |
| 4,863,477 A | 9/1989 | Monson | |
| 4,904,260 A * | 2/1990 | Ray et al. ................. | 623/17.12 |
| 5,047,055 A * | 9/1991 | Bao et al. ................. | 623/17.16 |
| 5,458,643 A * | 10/1995 | Oka et al. ................. | 623/17.16 |
| 5,534,028 A * | 7/1996 | Bao et al. ................. | 623/17.16 |
| 5,549,679 A * | 8/1996 | Kuslich ................... | 623/17.12 |
| 5,571,189 A | 11/1996 | Kuslich | |
| 5,645,597 A * | 7/1997 | Krapiva ..................... | 606/279 |
| 5,674,295 A * | 10/1997 | Ray et al. ................. | 623/17.12 |
| 5,976,186 A * | 11/1999 | Bao et al. ................. | 623/17.16 |
| 6,099,565 A * | 8/2000 | Sakura, Jr. ................ | 623/8 |
| 6,165,225 A * | 12/2000 | Antanavich et al. ....... | 623/23.72 |
| 6,224,630 B1 * | 5/2001 | Bao et al. ................. | 623/17.16 |
| 6,231,609 B1 * | 5/2001 | Mehdizadeh .............. | 623/17.11 |
| 6,264,695 B1 * | 7/2001 | Stoy ......................... | 623/17.16 |
| 6,419,704 B1 * | 7/2002 | Ferree ...................... | 623/17.12 |
| 6,443,988 B2 | 9/2002 | Felt et al. | |
| 6,482,234 B1 * | 11/2002 | Weber et al. ............. | 623/17.12 |
| 6,607,544 B1 | 8/2003 | Boucher et al. | |
| 6,613,089 B1 | 9/2003 | Estes et al. | |
| 6,620,196 B1 * | 9/2003 | Trieu ....................... | 623/17.16 |
| 6,726,721 B2 * | 4/2004 | Stoy et al. ................ | 623/17.16 |
| 6,733,533 B1 * | 5/2004 | Lozier ..................... | 623/17.12 |
| 6,758,863 B2 * | 7/2004 | Estes et al. ............... | 623/17.16 |
| 6,764,514 B1 * | 7/2004 | Li et al. ................... | 623/17.12 |
| 6,783,546 B2 * | 8/2004 | Zucherman et al. ...... | 623/17.16 |
| 7,001,431 B2 | 2/2006 | Bao et al. | |
| 7,060,100 B2 | 6/2006 | Ferree et al. | |
| 7,077,865 B2 * | 7/2006 | Bao et al. ................ | 623/17.12 |
| 7,172,628 B2 * | 2/2007 | Lamprich et al. ........ | 623/17.16 |
| 7,252,685 B2 * | 8/2007 | Bindseil et al. .......... | 623/16.11 |
| 7,318,840 B2 * | 1/2008 | McKay .................... | 623/17.11 |
| 2002/0049498 A1 * | 4/2002 | Yuksel et al. ............ | 623/17.12 |
| 2002/0077701 A1 * | 6/2002 | Kuslich ................... | 623/17.12 |
| 2002/0147496 A1 * | 10/2002 | Belef et al. .............. | 623/17.12 |

(Continued)

*Primary Examiner*—Alvin J Stewart
(74) *Attorney, Agent, or Firm*—McHale & Slavin, P.A.

(57) ABSTRACT

The present invention provides an implant for positioning within a particularly dimensioned body cavity. The implant is reversibly deformable between an expanded state and a compressed state. The implant is constructed and arranged for insertion within the body cavity when in its compressed state, and pressurelessly conforms to the cavity dimensions in its expanded state. Particularly, the implant is characterized by spontaneous deformation to the expanded state in situ within the body cavity while retaining and/or absorbing at least one flowable constituent as a function of its degree of deformation.

9 Claims, 4 Drawing Sheets

U.S. PATENT DOCUMENTS

| | | | |
|---|---|---|---|
| 2002/0183848 A1* | 12/2002 | Ray et al. | 623/17.12 |
| 2003/0040800 A1* | 2/2003 | Li et al. | 623/17.12 |
| 2003/0093152 A1* | 5/2003 | Pedersen et al. | 623/14.12 |
| 2004/0044412 A1* | 3/2004 | Lambrecht et al. | 623/17.16 |
| 2004/0098131 A1* | 5/2004 | Bryan et al. | 623/17.15 |
| 2004/0153064 A1* | 8/2004 | Foley et al. | 606/53 |
| 2004/0215344 A1* | 10/2004 | Hochschuler et al. | 623/17.12 |
| 2004/0249463 A1* | 12/2004 | Bindseil et al. | 623/17.16 |
| 2005/0010297 A1* | 1/2005 | Watson et al. | 623/17.12 |
| 2005/0015150 A1* | 1/2005 | Lee | 623/17.12 |
| 2005/0036946 A1* | 2/2005 | Pathak et al. | 424/9.4 |
| 2005/0065609 A1* | 3/2005 | Wardlaw | 623/17.12 |
| 2005/0090901 A1* | 4/2005 | Studer | 623/17.12 |
| 2006/0247780 A1* | 11/2006 | Bert | 623/17.16 |
| 2006/0253198 A1* | 11/2006 | Myint et al. | 623/17.12 |
| 2007/0073402 A1* | 3/2007 | Vresilovic et al. | 623/17.12 |
| 2007/0135921 A1* | 6/2007 | Park | 623/17.12 |
| 2008/0132934 A1* | 6/2008 | Reiley et al. | 606/192 |

* cited by examiner

REVERSIBLY DEFORMABLE IMPLANT

FIELD OF THE INVENTION

The invention generally relates to expandable implants; particularly, to a reversibly deformable implant constructed and arranged for ease of positioning within a body cavity wherein the implant pressurelessly expands in situ to substantially conform to the body cavity.

BACKGROUND OF THE INVENTION

As result of aging, disease and/or injury, the non-bony tissues disposed between adjacent bone structures can lose their resilience and shock absorbing characteristics which may result in pain and decreased range of movement in the affected area. For example, consider degenerative disc disease of the spine. The human spine is formed by an arranged column of bone structures (vertebra) separated by small cartilaginous cushions identified as intervertebral discs designed to absorb pressure (axial load) and keep the spine flexible. The disc contains a jelly-like nucleus pulposus surrounded by an outer ring of tough elastic ligament material that holds the vertebrae together, called the annulus fibrosus. As the disc degenerates, the nucleus and annulus becomes thinner and less able to handle axial loads. The annulus may begin to bulge (disc herniation) or rupture, narrowing the intervertebral disc space and impinging nerves within or adjacent to the spinal column, which may result in the individual experiencing pain of varying degree and manifestation, diminished flexibility, and reduced range of motion.

In order to reduce the pain associated with the movement of the intervertebral joint, surgical intervention is often indicated as a means to alleviate pressure upon the spinal cord while concomitantly stabilizing the associated vertebrae. This involves a surgical procedure to distract the disc, vertebra, or portions thereof, and insert intervertebral implants into the cavity created between the opposing vertebra to help support the spine and restore the normal spacing.

The most commonly used intervertebral devices are substantially rigid and manufactured at various preset heights requiring a cavity between opposing vertebrae be prepared and distracted to a dimension corresponding to the most suitably sized device. Some of these implants are hollow so that they may be packed with osteogenic material to ensure solid bone growth through and around the implant, fusing the two vertebrae. The surgical procedure to prepare the implant site can be difficult and lengthy. Moreover, the procedure requires the surgeon to create large incisions and passageways to the targeted disc space, resulting in increased recovery time, pain, and risk of trauma to the tissues surrounding the implant site.

Recently, expandable implants have been developed that may be used as both a fusion device and/or a means for maintaining intervertebral spacing. Often these implants are in the form of an expandable hollow cavity (balloon, bladder) in fluid communication with a fluid delivery means. The collapsed balloon is capable of being positioned within a disc cavity and expanded in situ by the introduction of fluid (gas, liquid) until the balloon is inflated to a size that corresponds to the cavity created when the damaged tissue is removed. The fluid delivery means typically includes a pressure monitoring component (e.g., pressure gauge, pressure sensor) used to determine when the balloon has reached the necessary size within the disc space. During the filling process, these types of systems must be carefully controlled lest the expanded balloon reaches a size or applies pressure in an amount that will overextend the disc cavity, creating additional injury to the surrounding tissue and/or bony surfaces.

DESCRIPTION OF THE PRIOR ART

Although there are numerous patents directed to expandable implant devices for insertion within a body cavity, the prior art nevertheless fails to teach a reversibly deformable implant capable of absorbing and/or retaining constituents (e.g., bone growth/fusion material, medication, curing material, etc.) within the device, while providing an individualized best fit inside the body cavity.

For example, U.S. Pat. No. 6,613,089 to Estes et al., relates to intervertebral spacers for use in orthopedic treatment of spinal defects. The intervertebral space is a shape memory polymer with a hollow cavity for the receipt of osteogenic material. The spacer can be fabricated into a desired configuration or deformed configuration by heating it above its deformation temperature ($T_d$) and then applying positive pressure or forcing it into a mold. The deformed spacer is then effectively frozen into its deformed conformation for implantation into a prepared disc space between adjacent vertebrae. After implantation into the prepared disc space, the deformed spacer is then heated directly or indirectly above its deformation temperature by application of a heating tool or heated saline solution. Unlike the present invention, the design of this patent suffers in that the application of heat to the polymer often causes thermal necrosis, that is, the tissue surrounding the implant is damaged or destroyed and the implant fails. Moreover, the polymer cannot absorb and retain the osteogenic material evenly throughout the implant for enhanced fusion between opposing vertebrae, unlike the present invention.

U.S. Pat. No. 7,060,100 to Ferree et al., discloses an artificial joint or disc replacement having a pair of opposing endplate components, each attached to one of the upper and lower vertebrae, a cushioning component disposed between the endplate components, and a mechanism for coupling the cushioning component to one or both of the endplates. In the preferred embodiment, the cushioning component takes the form of a tire-like outer structure attached to an inner hub. A filler material is also preferably contained within the cushioning component. The filler material may be a gas, liquid, foam, or gel (hydrogel). One or both of the endplate components may include a modified surface to increase adherence to respective opposing bone surfaces. Unlike the present invention, the implant of Ferree et al., does not disclose collapsing the filler material to a reduced volume for insertion into the body cavity, whereupon the implant is spontaneously deformed to its expanded state such that the constituents are evenly distribution throughout the implant without the possibility of overextending the implant.

U.S. Pat. No. 7,001,431 to Bao et al., and U.S. Pat. No. 6,443,988 to Felt et al., both disclose a system for repairing an intervertebral disc by delivering and curing a biomaterial in situ, within the disc. The system includes both a device, having an insertable balloon and related lumen, controls and adapters, as well as a curable biomaterial (and related biomaterial delivery means). The system relies on the doctor to determine a suitable endpoint for biomaterial delivery, by controlling distraction and/or biomaterial delivery pressure, and in turn, to deliver a desired quantity of biomaterial to the balloon in order to achieve improved polymer cure and implant characteristics. Also provided is a related method for repairing an intervertebral disc by using such a system to deliver and cure the biomaterial in situ. The system can be used to implant a prosthetic total disc, or a prosthetic disc nucleus in a manner that leaves the surrounding disc tissue substantially intact. These references suffer in that the expanded balloon can easily reach a size that will can over-extend the disc cavity possibly creating additional injury to the surrounding tissue and/or bony surfaces.

U.S. Pat. No. 5,571,189 to Kuslich is drawn to an expandable, porous fabric implant for insertion into the interior of a prepared disc space to stabilize the spinal segment. The fabric pores allow for tissue ingrowth through the implant. Unlike present invention, the implant of Kuslich must be positioned with the fill opening available to the surgeon inside the disc space, so that the surgeon can close the opening. Also, this patent also has the same drawbacks as balloon type implants, that is, the balloon can be easily overfilled, possibly damaging the surrounding tissue and/or bone.

U.S. Pat. No. 6,607,544 to Boucher et al., discloses an expandable balloon structure designed to compress cancellous bone within the vertebral body to form an interior cavity that can be used to receive filling material. The expandable structure is made from a non-porous elastomer material that is preformed to a desired geometry by exposure to heat and pressure. The structure undergoes expansion and further distension under application of positive pressure when placed inside the cancellous bone.

While the foregoing described prior art implants may have advanced the surgical art in a variety of ways, there nevertheless remains a need for a resilient implant capable of being reversibly deformed between an expanded state and a compressed state which utilizes differential pressure to introduce at least one flowable constituent (e.g., bone fusion material, medication, curing material, etc.) within interstices of the implant for enhanced fusion between adjacent bony surfaces without the possibility of overextending the implant and causing damage to neighboring structures.

SUMMARY OF THE INVENTION

The instant invention is related to a reversibly deformable biocompatible member (also referred to as an implant) suitable for positioning within a particularly dimensioned body cavity. The resilient member is reversibly deformable between a first expanded state and a compressed state. Moreover, the resilient member is characterized by spontaneous deformation to its expanded state absent any pressure. The resilient member is constructed and arranged to retain and/or absorb at least one desired constituent, as a function of its degree of deformation. The resilient member functions as a depot for the administration and/or retention of the desire constituents within the body cavity. Additionally, the resilient member is constructed and arranged for insertion within the body cavity when in its compressed state, and pressurelessly conforms to the cavity in the expanded state.

It is therefore an objective of the instant invention to provide a reversibly deformable member, kit and method for stabilizing a body cavity.

Another objective of the present invention is to disclose a resilient member formed from a reticulated biocompatible material that permits flowable constituents to permeate throughout while concomitantly allowing the ingrowth of tissue from the surrounding body cavity.

Still another objective of the present invention is to provide a reversibly deformable implant device which requires only a small entrance incision and narrow passageways for implantation, thereby reducing stress and healing time for the patient.

Yet another objective of the present invention is to teach an implant that could be used for support for partial or total joint replacements, that is, the implant of the present invention could be used in cancellous bone for the fixation of fractures or other osteoporotic and non-osteoporotic conditions of human and animal bones.

These and other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Detailed embodiments of the instant invention are disclosed herein, however, it is to be understood that the disclosed embodiments are merely exemplary of the invention, which may be embodied in various forms. Therefore, specific functional and structural details disclosed herein are not to be interpreted as limiting, but merely as a basis for the claims and as a representation basis for teaching one skilled in the art to variously employ the present invention in virtually any appropriately detailed structure.

In general, this invention provides an implant formed for stabilizing a targeted area (e.g., body cavity). The resilient member or implant is formed from a reversibly deformable biocompatible member 2, see cross-sectional profiles of FIGS. 1-4. The implant may be formed to any desired shape, size, or it may be amorphous. The size and dimensions of the implant will be chosen based on the anatomy of different sexes, age and region of the body (spine, knee, hip, etc.) being targeted.

Moreover, the implant is constructed and arranged such that it is able to reversibly deform from a compressed state to an expanded state. The implant can be readily deformed to its compressed state having a reduced cross-sectional profile and/or reduced volume (see FIG. 2). When in the compressed state, the member may be inserted to the desired body cavity 8, shown here between two opposing vertebrae 4, 6, through an incision smaller than the implant in its expanded state, using any minimally invasive technique known to those having skill in the art (e.g., laparoscopic, endoscopic, etc.)

Figure 2:
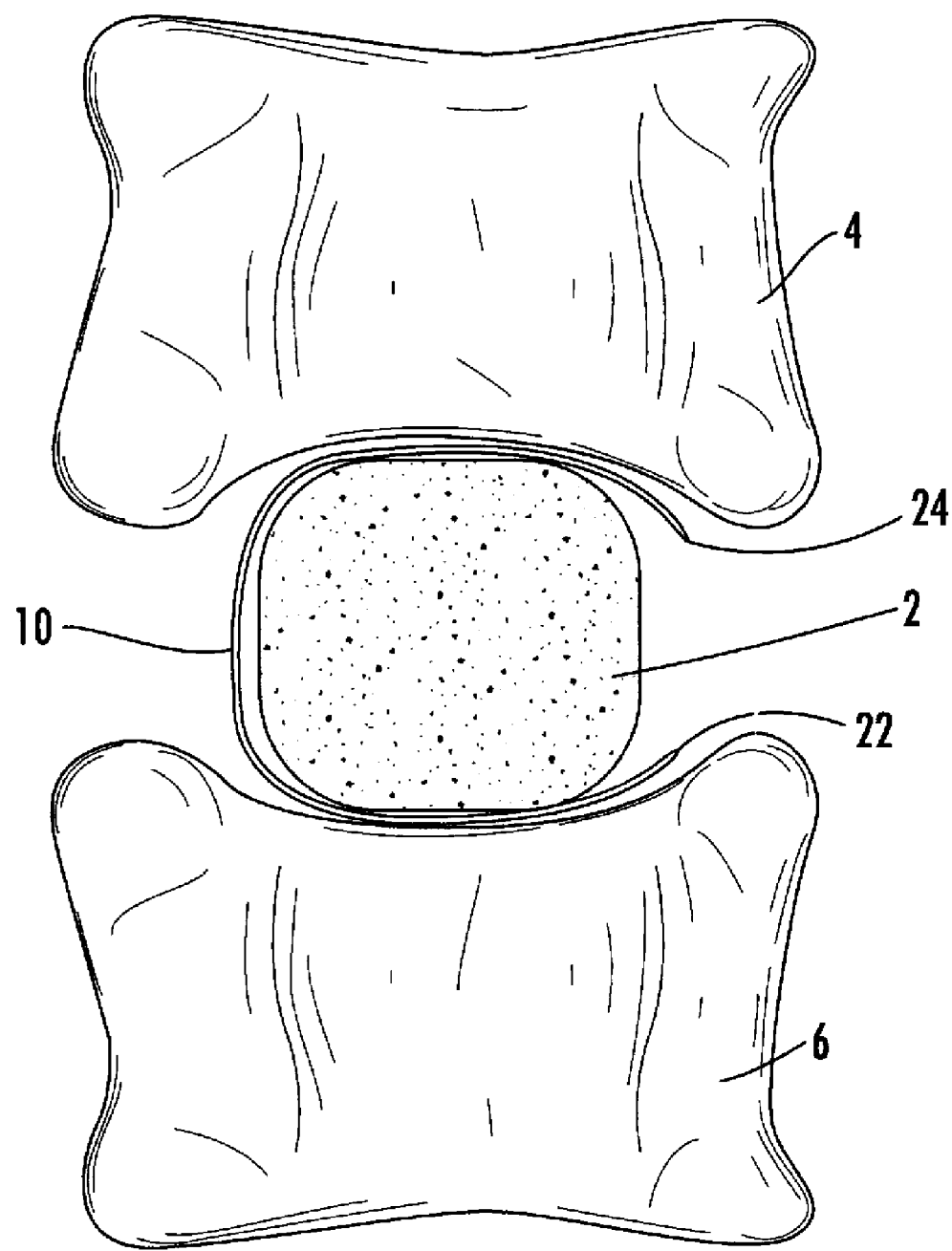
FIG. 2 is an axial cross-sectional view of the reversibly deformable implant device shown in its expanded state inside the body cavity.

Once inside the body cavity, the resilient member is able to expand without the application of pressure or temperature, to substantially conform to the dimension of the body cavity (FIG. 2). The implant should be sufficiently strong as to maintain the desired space between the bone structures once expanded. Moreover, while expanding, the implant can absorb and retain at least one desired constituent as a function of its degree of deformation; that is, the more implant expands the more constituent can be absorbed and/or retained therein.

According to one particularly preferred embodiment, the implant is formed from a reticulated biocompatible material, which includes multiple pores or voids formed uniformly throughout the member. The size and density of the pores should substantially retain fluid introduced therein, while concomitantly permitting the ingrowth of surrounding tissue therein. Non-limiting examples of suitable a reversibly deformable member might include autograph, allograft, other osteobiologic tissue, or combinations thereof.

Figure 1:
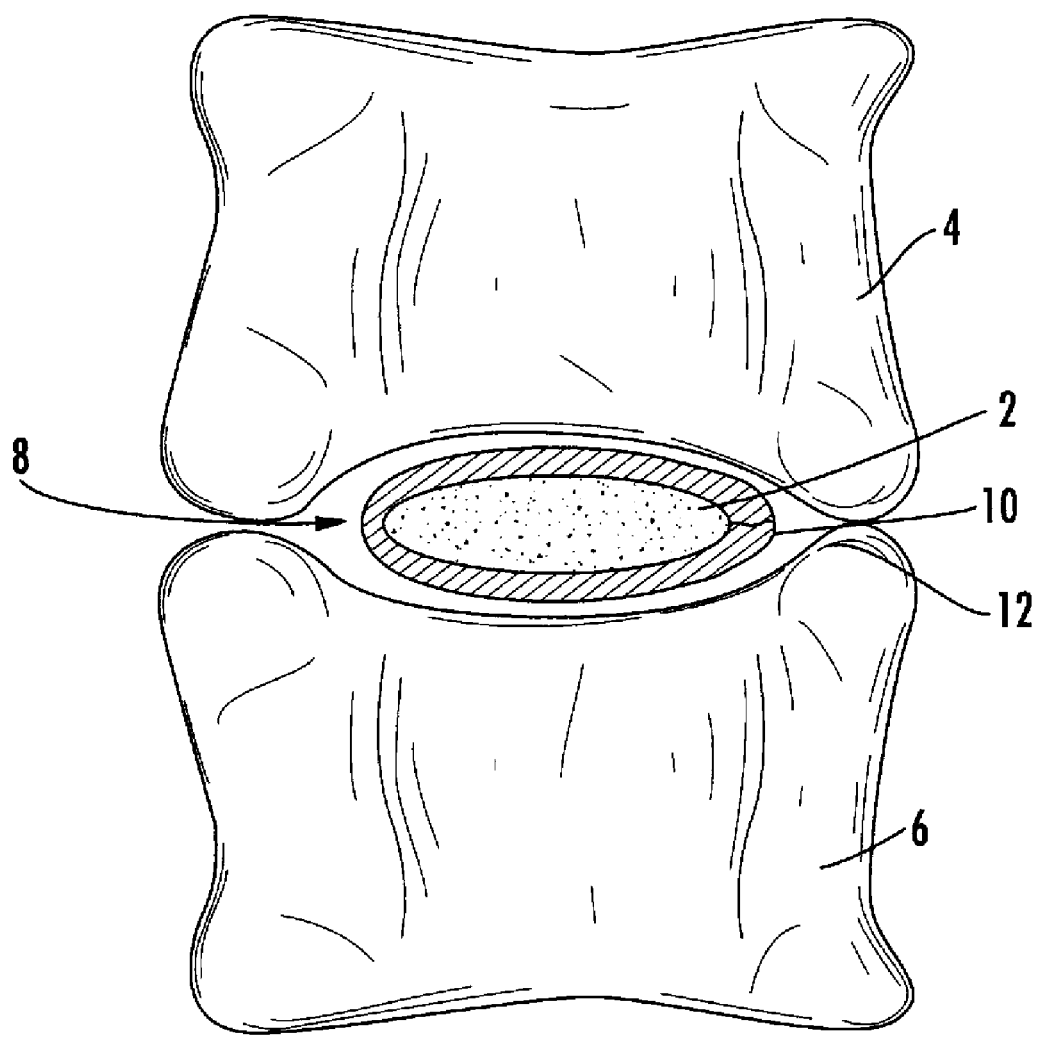
FIG. 1 is an axial cross-sectional view of a reversibly deformable implant shown in its compressed state inside a body cavity disposed between opposing vertebrae according to the present invention.

According to one non-limiting, illustrative embodiment shown in FIGS. 1-2, the implant may be placed inside a containment means 10 capable of sustaining a vacuum environment therein. The containment means should be inert or made from any bioresorbable material known in the art, discussed further below. The implant is deformed into a compressed state by a vacuum source. Under vacuum, the outer package essentially conforms to and maintains the compressed shape of the implant. The evacuated package also includes therein one or a mixture of flowable constituents 12.

Figure 4:
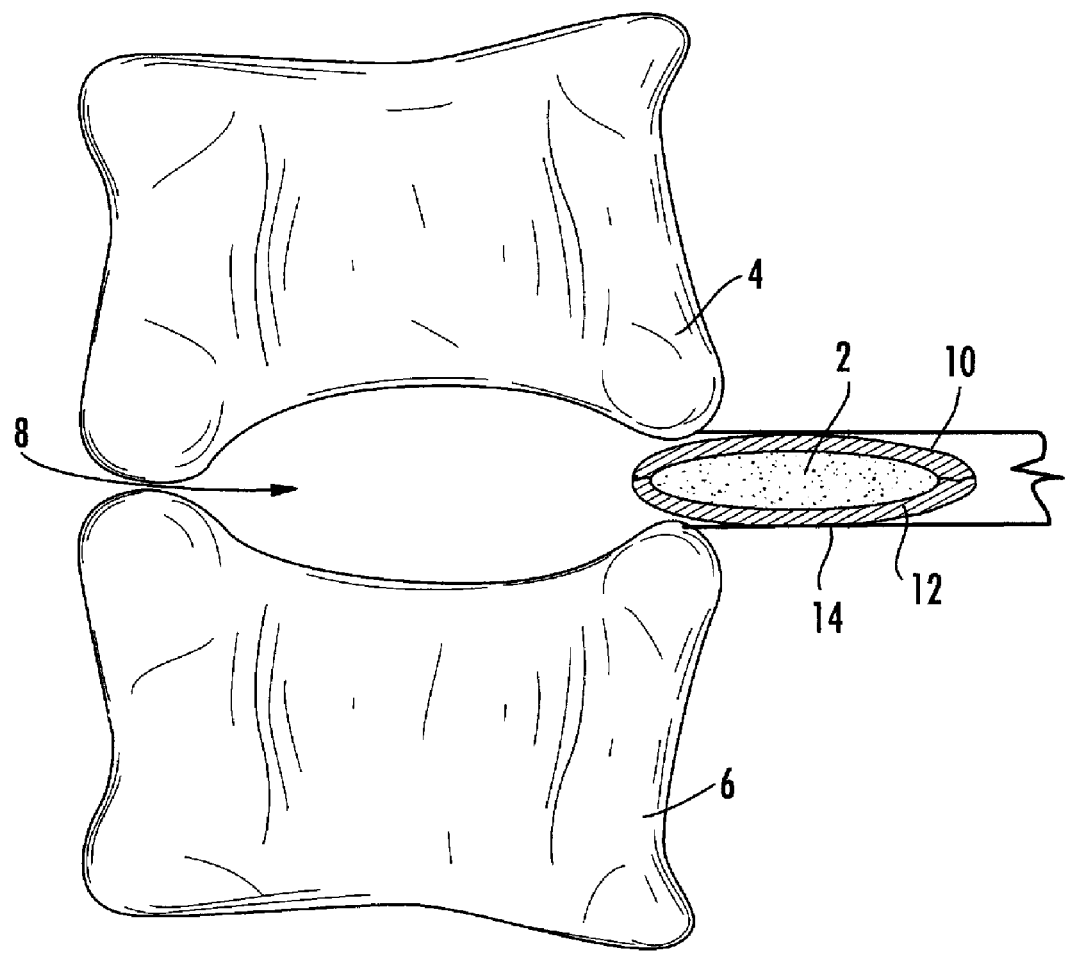
FIG. 4 is an axial cross-sectional view of the reversibly deformable implant device shown in its compressed state inside an introduction means used to insert the implant into the body cavity.

As discussed above, the compressed implant is readily passed through the previously prepared narrow incision and channels and into the prepared body cavity by any suitable insertion tool known in the art. The compressed implant is capable of being readily inserted into the distal end of a conventional insertion device 14. For example, as shown in FIG. 4, the compressed implant is removably inserted into the distal end of a cannula.

Once the implant is positioned inside the prepared cavity, the containment means 10 is ruptured in situ, see ruptured ends 22, 24 of containment means shown in FIG. 2. The release of the vacuum inside the compressed implant causes the spontaneous deformation of the member to its expanded state (FIG. 2). This pressure sink in the implant spontaneously causes the constituents inside the containment means to flow into the implant until the member is reformed to its expanded state or the sides of the implant substantially conform to the anatomy of the body cavity, thereby helping to restore the original spacing and/or stabilize the cavity between the adjacent bone structures without over extending the cavity.

The use of a vacuum to fill the implant will spontaneously distribute constituents throughout the interstices formed therein. After the implant is in situ, the containment means could be removed or the containment means could be made from a bioresorbable material and left inside the cavity to harmlessly absorb into the body. The term "bioresorbable material" is intended to encompass any non-toxic, non-immunogenic material, natural or synthetic, capable of being formed into a package which after insertion is gradually hydrolyzed and absorbed over a finite period of time by chemical/biological activity in the body. Illustrative, albeit non-limiting, examples are polylactic acid, polyglycolic acid, polycaprolactone, polyanhydrides, polydioxanone, polyamino acids, trimethylene carbonate, 1,5-dioxepan-2-one, copolymers of lactic acid, hydroxyapatite and alginates. Commercially available bioresorbable materials such as LACTOSORB (Walter Lorenz Surgical, Inc. Jacksonville, Fla.) could be used.

It is contemplated that the implant might be constructed and arranged to deform into its compressed state for a period of time after application of a vacuum source (not shown) directly thereto, without the need for containment means. Furthermore, it is contemplated that any means for creating a negative pressure (vacuum) inside the containment means could be used herein without departing from the scope of the invention. The vacuum source could be employed during the manufacturing process to create a negative pressure inside the containment means.

Alternatively, a kit might be supplied to the surgeon which includes at least one containment means, at least one implant, and optionally, at least one desired constituent. The surgeon could apply an available vacuum source to containment means (or implant) immediately prior to implantation. This is particularly desirable should the surgeon have specific flowable constituents in mind for introduction into the implant.

The flowable constituents used herein could include, albeit are not limited to, bone morphogenic proteins, bone growth factors, stem cell treatments, medication, platelet concentrations, bodily fluids, or the like.

Figure 3:
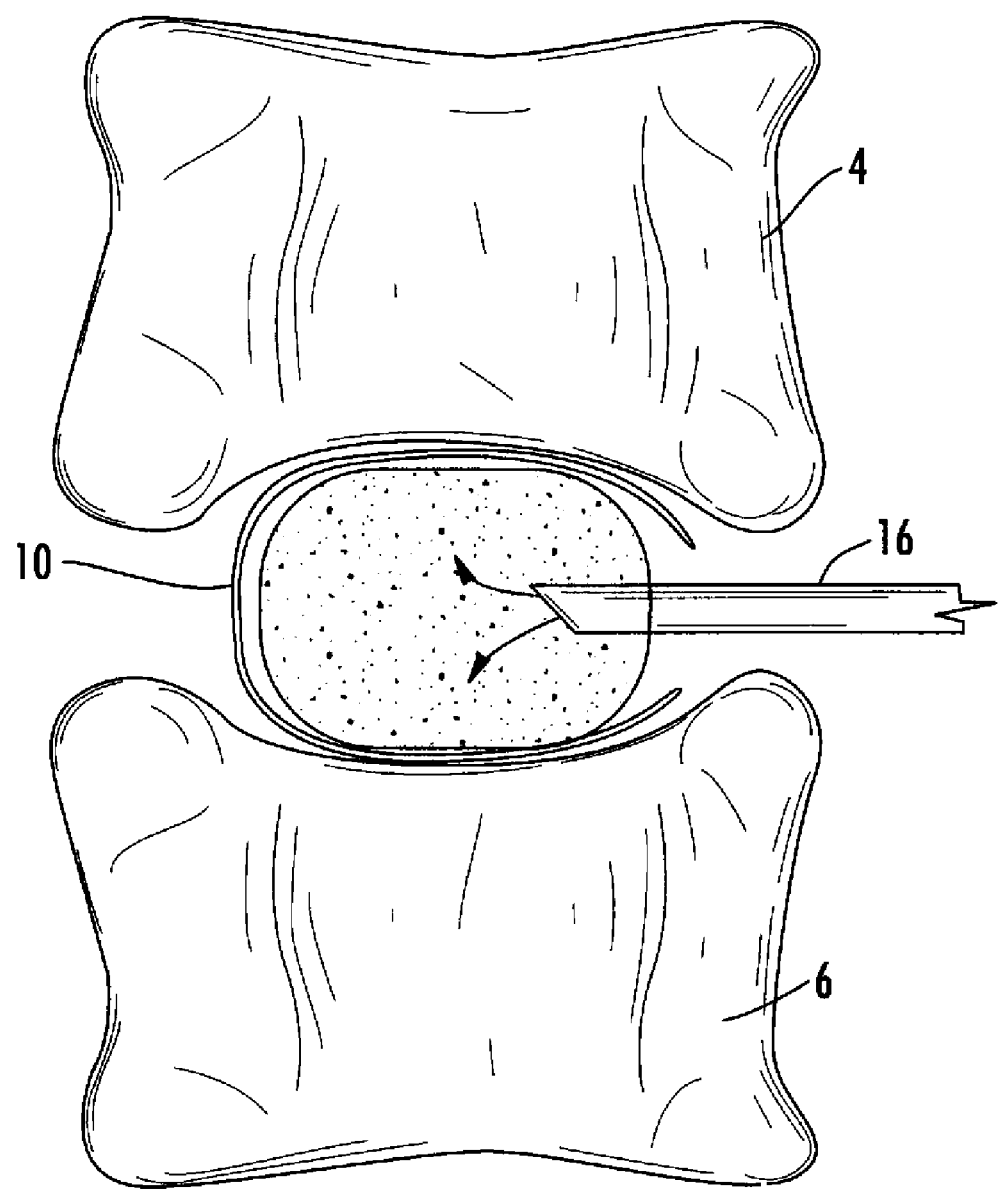
FIG. 3 is an axial cross-sectional view of the reversibly deformable implant device shown in its expanded state wherein additional constituents are being added.

Moreover, additional flowable constituents might be introduced into the expanded implant inside the targeted body region by any appropriate introduction means 16, such as, a cannula, lumen, or syringe, see FIG. 3. For example, additional constituents might include a hardening or curing agent.

According to yet another embodiment particularly suitable for treatment of osteoporotic compression fractions, the resilient member may be coated with at least one reactive constituent that reacts with the flowable constituents introduced into the implant. For example, the implant may be coated with a material whereupon introduction of a hardening agent by the introducing means 16 into the expanded implant would cause the implant to sufficiently harden so as to form a rigid internal cast, thereby arresting the motion cause by the fraction and restore the loss of height caused by the fracture. According to another embodiment, the resilient member may be coated with at least one time-released constituent that could provide for the continuous delivery of the concentrated constituents over time.

Although the invention is described with reference to stabilization and fusion of adjacent spinal vertebrae, it is hereby contemplated that devices and methods disclosed herein could be used in all types of joints (knee, ankle, etc) found in the human or animal body.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A reversibly deformable biocompatible implant suitable for positioning within a particularly dimensioned body cavity, comprising:

a substantially resilient porous state member formed from a reticulated material having a plurality of deformable cavities, said deformable cavities having resilient walls, said substantially resilient porous state member is reversibly deformable between a first expanded state and a second compressed state, said first expanded state being larger in volume than said second compressed state, said deformable cavities being reduced in size as the resilient walls are compressed in said second compressed state;

a containment member surrounding and completely enclosing said substantially resilient porous state member, the complete enclosure of said containment member over said substantially resilient porous state member maintains a vacuum only when said substantially resilient porous state member is in said second compressed state;

said containment member is ruptured in situ creating ruptured ends to release the vacuum inside the compressed substantially resilient porous state member and causes the spontaneous deformation of said substantially resilient porous state member to its expanded state;

said substantially resilient porous state member and said containment member are sized and configured for insertion within said body cavity when said substantially resilient porous member second is in said compressed state and enclosed within said containment member, and said substantially resilient porous state member conforms to said body cavity dimensions in said first expanded state upon rupture of said containment member subsequent to placement of both members within said body cavity.

2. A reversibly deformable biocompatible implant suitable for positioning within a particularly dimensioned body cavity, comprising:

a substantially resilient porous state member formed from a material having a plurality of deformable cavities, said plurality of cavities having resilient walls, said substantially resilient porous state member being reversibly deformable between a first expanded state and a second compressed state, said first expanded state being larger in volume than said second compressed state, said deformable cavities being reduced in size as the resilient walls are compressed in said second compressed state;

a containment member surrounding and completely enclosing said substantially resilient porous state member, the complete enclosure of said containment member over said substantially resilient porous state member maintains a vacuum only when said substantially resilient porous state member is in said second compressed state;

said containment member is ruptured in situ creating ruptured ends to release the vacuum inside the compressed substantially resilient porous state member and causes the spontaneous deformation of said substantially resilient porous state member to its expanded state;

said substantially resilient porous member containing at least one flowable constituent as a function of its degree of deformation in situ, said resilient porous state member functions as a depot for administration and/or retention of said at least one constituent within said body cavity;

said substantially resilient member and said containment member are sized and configured for insertion within said body cavity when said substantially resilient member is in said second compressed state and enclosed within said containment member, and said substantially resilient porous state member conforms to said body cavity dimensions in said first expanded state upon rupture of said containment member subsequent to placement of both members within said body cavity.

3. The implant as set forth in claim 2, wherein said substantially resilient porous state member is formed from a reticulated biocompatible material such that said at least one constituent is distributed substantially evenly through said substantially resilient porous state member.

4. The implant as set forth in claim 2, wherein said flowable constituent includes at least one member selected from the group consisting of; bone morphogenic proteins, bone growth factors, stem cell treatments, platelet concentrations, and medication.

5. The implant as set forth in claim 2, wherein said substantially resilient porous state member is coated with an additional constituent.

6. A kit comprising:

at least one flowable constituent; and at least one substantially resilient porous state member formed from a material having a plurality of deformable cavities, said deformable cavities having resilient walls, said at least one substantially resilient porous state member is reversibly deformable between a first expanded state and a second compressed state, said first expanded state being larger in volume than said second compressed state, said deformable cavities being reduced in size as the resilient walls are compressed in said second compressed state;

a containment member surrounding and completely enclosing said substantially resilient porous state member, the complete enclosure of said containment member over said substantially resilient porous state member maintains a vacuum only when said substantially resilient porous state member is in said second compressed state;

said containment member is ruptured in situ creating ruptured ends to release the vacuum inside the compressed substantially resilient porous state member and causes the spontaneous deformation of said substantially resilient porous state member to its expanded state;

said substantially resilient porous state member containing at least one flowable constituent as a function of its degree of deformation in situ for administration and/or retention of said at least one constituent within said body cavity;

said substantially resilient porous state member and said containment member are sized and configured for insertion within said body cavity when substantially resilient member is in said second compressed state and enclosed within said containment member and returns to its first expanded state to substantially conform to said body cavity upon rupture of said containment member subsequent to placement of both members within said body cavity.

7. The kit as set forth in claim 6, wherein said substantially resilient porous state member is formed from a reticulated biocompatible material such that said at least one constituent is distributed substantially evenly through said substantially resilient porous state member.

8. The kit as set forth in claim 6, wherein said flowable constituent includes at least one member selected from the group consisting of; bone morphogenic proteins, bone growth factors, stem cell treatments, platelet concentrations, and medication.

9. The kit as set forth in claim 6, wherein said substantially resilient porous state member is coated with an additional constituent.

* * * * *